United States Patent [19]

Zelnigher

[11] Patent Number: 4,501,556
[45] Date of Patent: Feb. 26, 1985

[54] APPARATUS AND METHOD FOR FABRICATION OF DENTAL PROSTHESES

[76] Inventor: Joseph Zelnigher, 310 W. 47th St., New York, N.Y. 10036

[21] Appl. No.: 477,924

[22] Filed: Mar. 23, 1983

[51] Int. Cl.³ .............................................. A61C 11/00
[52] U.S. Cl. ...................................... 433/56; 433/60; 433/63; 433/65
[58] Field of Search ....................... 433/54, 55, 56, 57, 433/58, 59, 60, 61, 62, 63, 64, 65, 66, 67

[56] References Cited

U.S. PATENT DOCUMENTS

| | | | |
|---|---|---|---|
| 198,853 | 1/1878 | Oehlecker | 433/57 |
| 1,614,828 | 1/1927 | Coffin | 433/60 |
| 2,376,384 | 5/1945 | Ringle et al. | 433/60 |
| 2,521,599 | 9/1950 | Neil | 433/57 |
| 2,841,871 | 7/1958 | Miller | 433/60 |
| 2,865,102 | 12/1958 | Zelnigher | 433/58 |
| 2,959,857 | 11/1960 | Stoll | 433/55 |
| 4,083,114 | 4/1978 | Acevedo | 433/55 |
| 4,278,426 | 7/1981 | Schwartz | 433/54 |

FOREIGN PATENT DOCUMENTS 2440731  7/1980  France ................................. 433/60

Primary Examiner—John J. Wilson
Attorney, Agent, or Firm—Lackenbach, Siegel, Marzullo, Presta & Aronson

[57] ABSTRACT

A device for use with an articulator in the construction of artificial dentures, comprising a base adapted to be placed on the articulator, a tabletop on the base, the height of which is adjustable; and a removable template adapted to be pivotably mounted to a cradle provided in said tabletop. A knife edge unit with spaced apart knife edges, and a spear box and pointer adapted to be raised or lowered by means of a ramp and associated adjustment screw is removably attached to said base in a manner such that said spear box is guided for movement along said ramp by threaded means in simultaneously both upward and forward directions, and the pointer being adapted to retain in place thereon an upper rim impression and tray prior to its being mounted to an upper mounting ring of the articulator.

14 Claims, 25 Drawing Figures

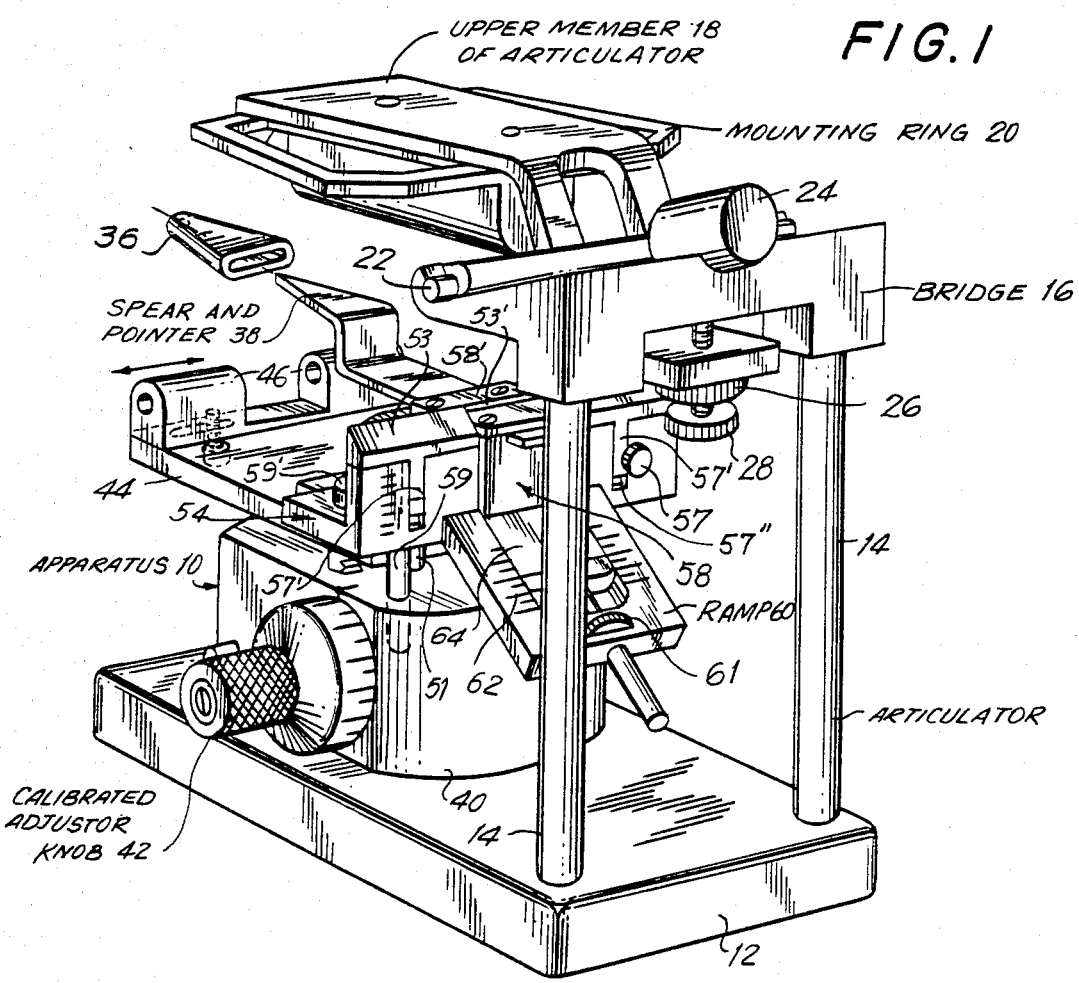

APPARATUS AND METHOD FOR FABRICATION OF DENTAL PROSTHESES

This invention relates to an apparatus and method for the fabrication of dental prostheses.

BACKGROUND AND SUMMARY OF THE INVENTION

The invention is a significant improvement over my U.S. Pat. No. 2,865,102, granted Dec. 23, 1958. In this patent, a "research" device is disclosed for fabricating prostheses comprising a holder upon which a maxillary cast is mounted, and positioning means are employed whereby the cast may be positioned for mounting on the holder. The positioning means is provided with knife edge for providing co-level support to specific points in the hamular notches of the maxillary cast and a sliding metal strip which extends normal to the knife edge for supporting the anterior midpoint portion of the maxillary cast. The positioning means may take the form of a plurality of points with two of the points being co-level for engagement with the points in the hamular notches of the cast.

In the prior art device which utilized fixed anatomical points for mounting the cast, the three points (hamular notches and mid point on the crest of the ridge at the front of the cast) were all positioned at the same elevation. Although my earlier device embodied some flexibility, such as in vertically and angularly positioning of a curved or flat template, considerable time and skill as well as experience was still required to fabricate dentures.

With the apparatus of my present invention, less skill and time are required. Moreover, with the improved apparatus, greater precision is achieved and the apparatus lends itself to wider use. The resulting cast orientation and/or setting of teeth are replicable at all times.

As a result of my development and research work with the aforesaid device, it was recognized that due to varying length of the anterior teeth, the three points are not on the same plane. This led to my further improvement of utilizing a spear-like element to raise or lower, as well as translate the tray and occlusion rim that holds the maxillary cast. In this arrangement of the device, the front or anterior point thus became independent of the rear or posterior points which are also capable of being raised or lowered. Such specifications further led to my uniquely movable knife edge assembly and mounting sleeve arrangement. When the mounting sleeve, attached to a tray with occlusion rim is impaled on the spear like element, the anterior point exhibits a 3° slope from the knife edge.

The anterior point resides at the mid-saggital plane of one's head. The replicability of results enables one to reproduce the exact fabrication of lost dentures after making duplicate casts from the original casts. The duplicates are maintained by the dentist or laboratory technician. In another application of my invention, it will be readily recognized that an orthodontist can observe his or her progress and progression in the redirecting and straightening of crooked or otherwise protruding teeth.

It is, therefore, the principal object of the invention to provide a device whereby an improved apparatus and method may be used in the fabrication of various types of dental prostheses.

Another object of the invention is to provide an improved apparatus or device which is simple in operation and yet extremely precise in its function and applicability to dental prostheses.

Yet a further object of the invention is to provide a device which can be transferred to an articulator with minimum effort, but with exact relationship.

It is yet another object of the invention to enable my improved device to be readily adapted for use on any dental articulator with or without the requirement of an intervening mounting plate or unit.

Accordingly, these and other objects of my invention will become readily apparent from a reading of the disclosure when taken in consideration of the accompanying drawings.

BRIEF DESCRIPTION OF THE DRAWINGS

The accompanying drawings, which are incorporated in and constitute a part of this specification, illustrate an embodiment of the invention and, together with the description serve to explain the principles of the invention, which are a means to orient the maxillary cast on the articulator in relationship to the opening axis of the temporomandibular joints, and to provide calibrations which make for replicability and precision.

FIG. 1 is a perspective view of an apparatus embodying the invention situated on the base of an articulator;

FIGS. 2 and 3, respectively, are a fragmentary perspective view and side elevational view of a ridge-lap ruler used in connection with measuring low lip line at the time of making the preliminary impressions;

DESCRIPTION OF THE PREFERRED EMBODIMENT

Figure 12:
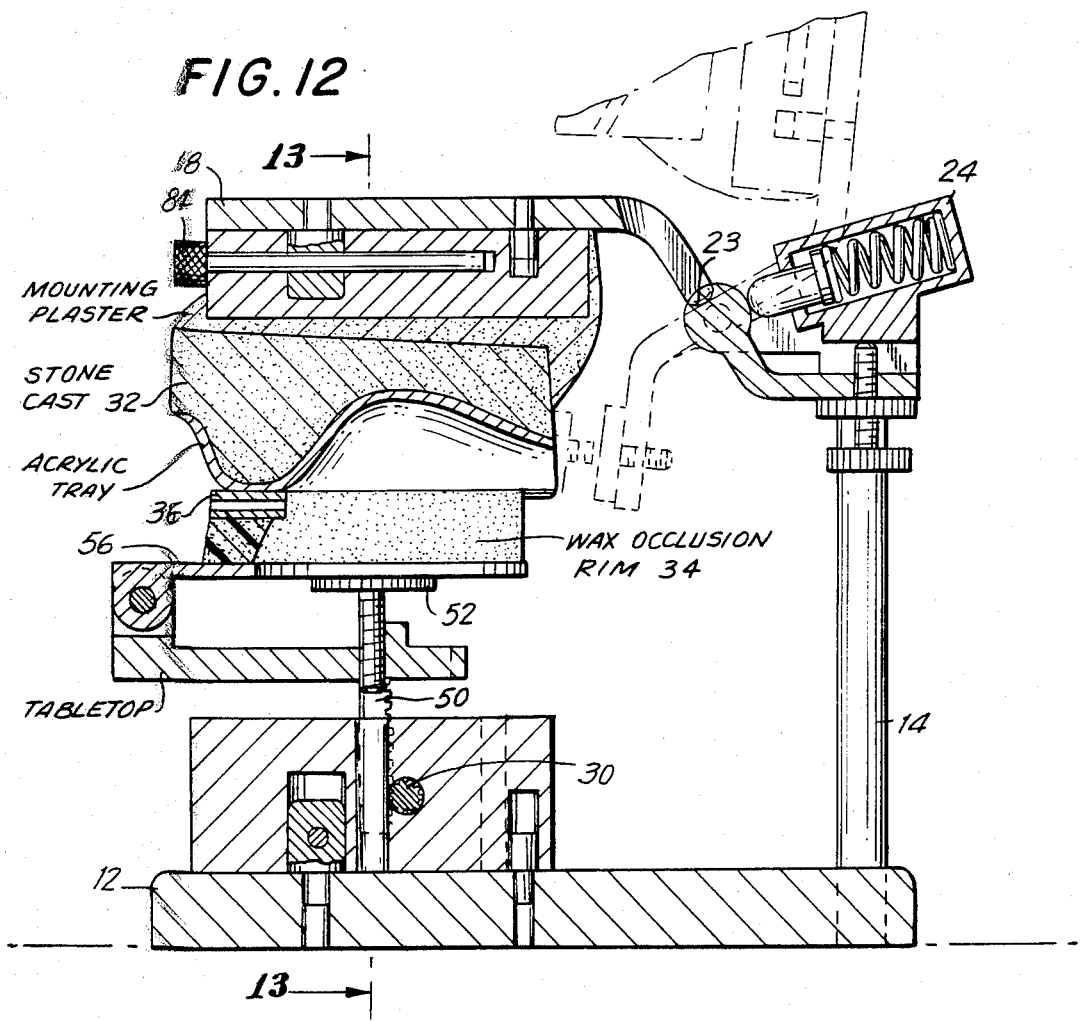
FIG. 12 is a cross-sectional view along the lines of 12—12 of FIG. 11.
Figure 19:
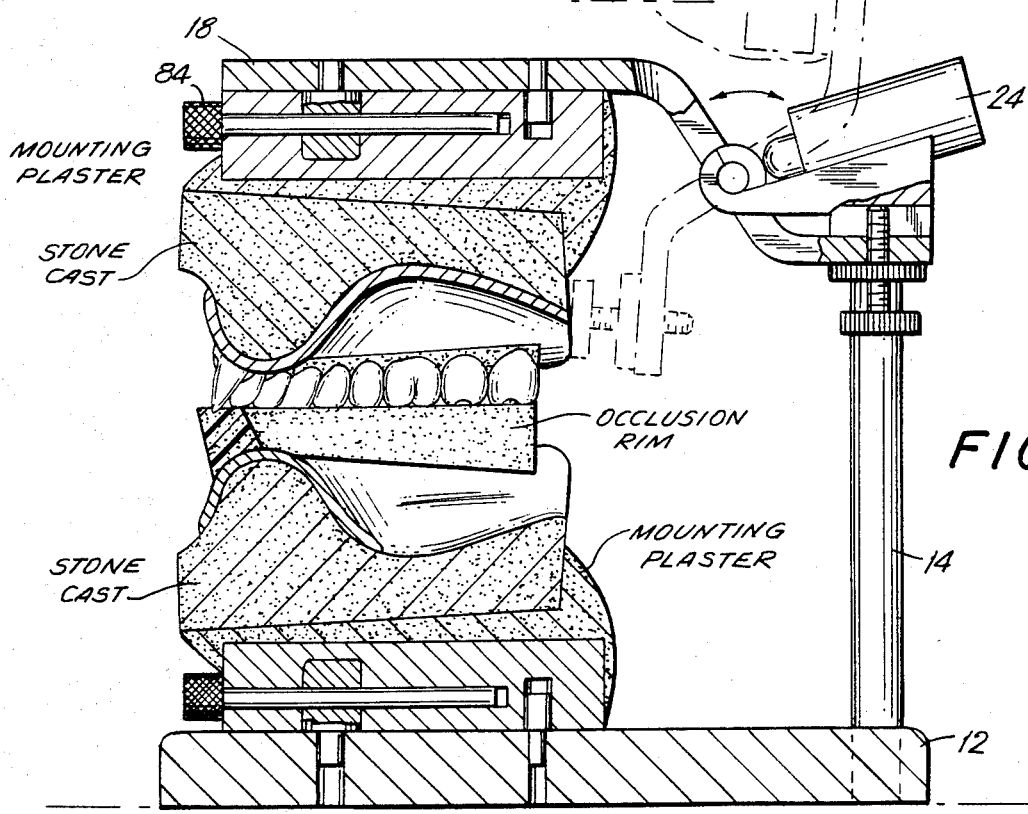
FIG. 19 is a sectional view taken along the line 19—19 of FIG. 17; showing the upper teeth set up on stone cast engaging the mandibular occlusion rim attached to the tray, resting on the lower stone cast.

Referring now to the drawings, and in particular to FIG. 1, there is shown my dental apparatus 10 for use in the fabrication and making of dental prostheses. As shown therein, such device is mounted on a conventional articulator base member 12, having a pair of vertical posts 14. Atop the vertical posts 14 is a bridge 16. An upper member 18 can simulate mandibular movement and holds a plate 20 which is used to mount a cast. FIGS. 12 and 19 show the upper member 18 and plate 20 with attached upper cast swung upwardly out of the way about the pin hinge 22. The spring-loaded plunger 24 engages dent 23 and so retains the upper element 18 and plate 20 in a locked upward position, as best shown in FIG. 12. The nut 26 and knurled screw 28 provide an adjustment capability for fine tuning the angle of the upper member 18 and plate 20, relative to the horizontal.

Figure 14:
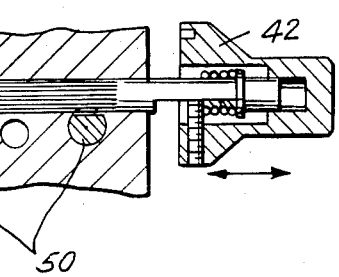
FIG. 14 is a cross-sectional view along the line 14—14 of FIG. 13.

Said apparatus 10 consisting of base 40 has a calibrated adjustor knob 42, as best shown in FIG. 14 for vertically adjusting the height of the tabletop 44 and template cradle 46 relative to the base 40. The cradle 46 is suitably mounted on the tabletop 44 by means of threaded means extending through suitable slots (one shown in FIG. 1) so that the cradle 46 may be shifted laterally to either side of the mid-line of the tabletop 44. In this manner, the mid-line of the template can be adjusted to fall on the clinical mid-line of the patient in the event that the clinical mid-line of the patient does not coincide with the mid-saggital line. The base 40 may be mounted on an articulator adaptor plate 48 as is necessary for certain articulators; (see FIG. 10) and the tabletop 44 is raised or lowered when the adjustor knob 42 is rotated (after being unlocked by an outward pull), thereby elevating or lowering the rod-like rack elements 50 supporting the tabletop 44. The knife edge unit 54 is slid upon tabletop 44 until the two locating pins 51 engage the two cut outs 55 in tabletop 44 (see FIGS. 5 and 11). The knife edge unit 54 is held in position by two lock pins 59 which penetrate the knife edge unit and enter into base 40. The locating pins orient the knife edge unit to be perpendicular to the mid-saggital plane. Threaded and knurled headed screw 52 serves to function as a means to stabilize the knife edge unit 43 when the latter is mounted on the tabletop 44. This same screw also supports the template 56 at different inclinations. The sliding pointer box cover 58' is suitably provided with an internally mounted leaf spring (not shown) which is used to frictionally grip and permit the spear 38 to be moved horizontally with one's fingers to any desired position (see horizontal arrowheads in FIGS. 5-6). The knife edge assembly 54 consists of knife edges 53 and the ramp 60 with a screw wheel 61 for driving the sliding plate 64 up and down. Pointer box 58 is one piece with sliding plate 64. When sliding plate is raised or lowered, the sliding pointer moves up and down too. Ramp 60 is suitably provided with markings 62 and there are provided index marks on the sliding plate 64. In this way, one can readily observe or compute the necessary adjustments or calibration readings to be taken by the dentist or dental technician.

In FIGS. 2 and 3, there is shown a ridge-lap ruler 66 for measuring the low lip line in millimeters directly on the patient. The yoke of the flexible ribbon-like metal end of the ruler represents a zero position and is positioned against the crest of the anterior ridge shown in FIG. 3, and the bottom of the lip 68 is read off the calibrations provided on the ruler 66. A caliper with a sliding index (not shown), disclosed in my earlier patent, may be employed. However, it is used to establish the "Low Lip Line" after a maxillary occlusion rim is constructed and carved to the Lower Lip Line with lip support. Then the caliper is used to measure the distance from ridge-lap to the Lower Lip Line on the occlusion rim.

Figure 4:
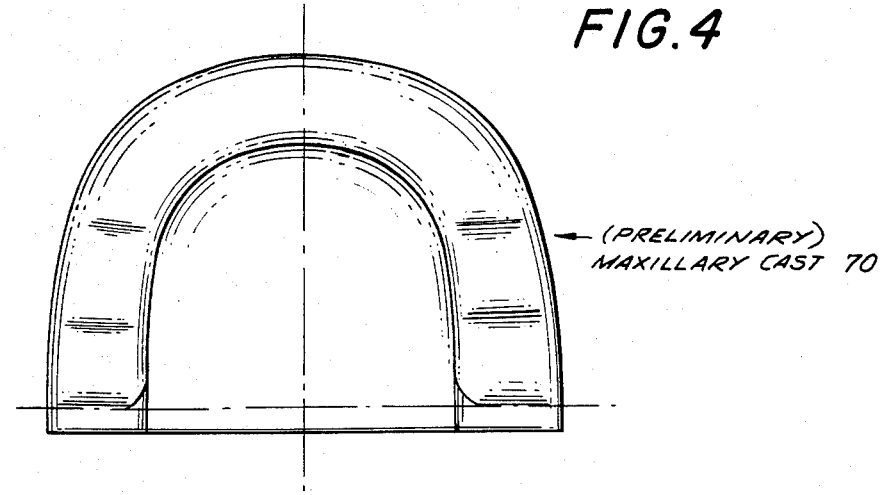
FIG. 4 is a plan view of a maxillary cast with the "cross-hairs" representing mid-saggital plane and horizontal plane reference lines.
Figure 5:
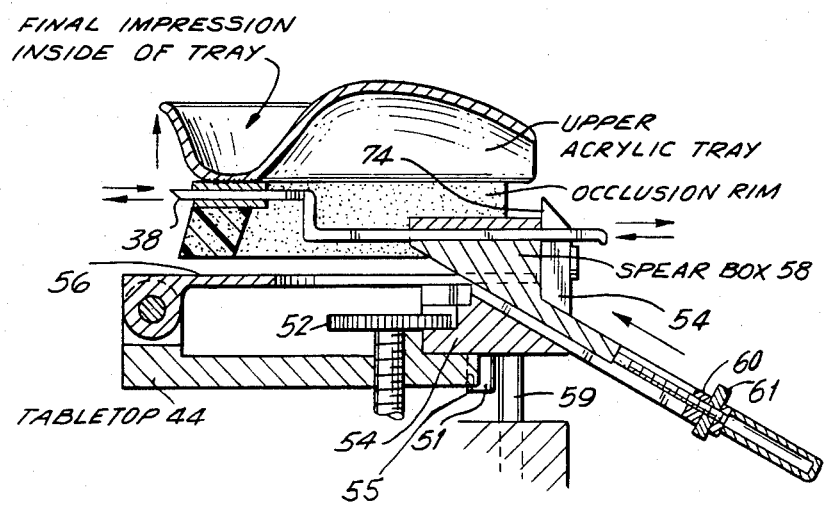
FIG. 5 is a cross-sectional view of the tabletop illustrating the ramp and sliding plate as well as the knife edge, and the tray with impression positioned on the sliding pointer spear.
Figure 6:
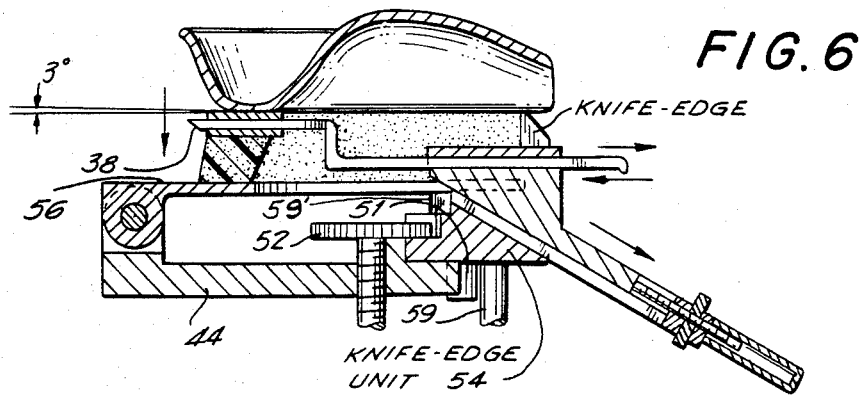
FIG. 6 is a cross-sectional view similar to that of FIG. 5, but showing the occlusion rim resting on the template which is horizontal and attached to the tabletop. The tip of said spear which is an extension of the midsagittal plane extends through and beyond the mounting sleeve.

A preliminary maxillary cast 70 is shown in FIG. 4, (the mandibular cast not being shown). This cast must reproduce the anatomy of the hamular notch area. FIG. 5 illustrates an acrylic tray made upon this preliminary cast. This tray contains a final impression of the patient's mouth. The tray has a mounting sleeve which is impaled upon sliding spear 38. It thus is suspended from the spear. The mounting sleeve 36 provides an aperture for the pointed end of the spear 38. FIG. 6 shows the acrylic tray with impression moved by means of the sliding pointer 38 together with box 58 and sliding plate 64 so that the occlusion rim may be placed anywhere along the inclined plane of the ramp or against the anterior facing wall 74 of the knife edge unit 54 with the pointer 38 along the mid-saggital plane, and with the occlusion rim resting on a template 56 chosen for the set up. Also, with the movement of the pointer to any given horizontal position, the occlusion rim can be readily positioned or located anywhere over the template as may be desired by the dentist or technician.

Figure 7:
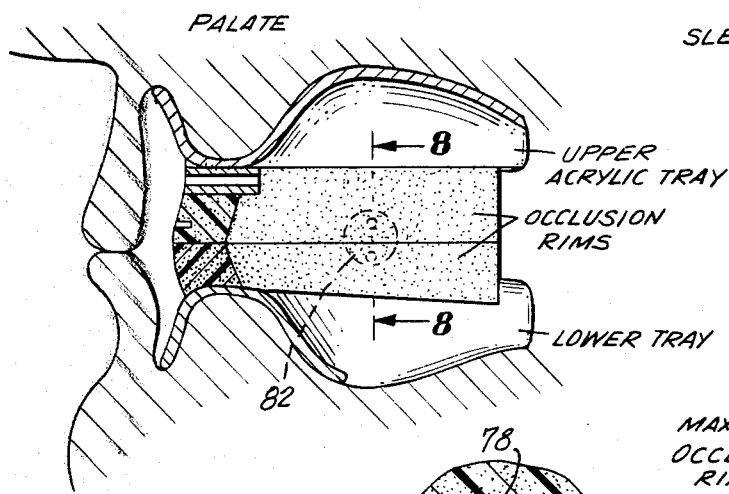
FIG. 7 is a side elevational view in cross-section illustrating both occlusion rims in the mouth; there is no mounting sleeve on lower tray.
Figure 7A:
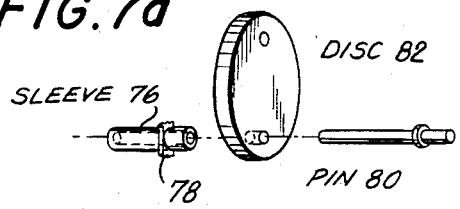
FIG. 7a is an exploded view of a locking disc or plate for holding together the upper and lower occlusion rims in a predetermined fixed position.
Figure 8A:
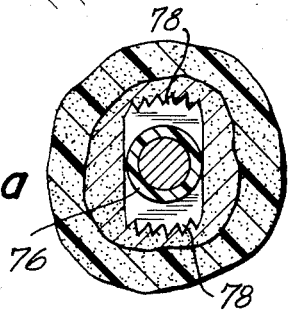
FIG. 8a is a fragmentary sectional view taken along the line 8a—8a of FIG. 8.
Figure 8:
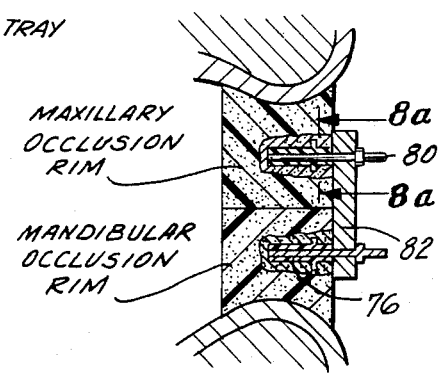
FIG. 8 is an enlarged fragmentary view in section taken along line 8—8 and through the locking plate shown in FIG. 7 which insures that both casts will be in the same position when reassembled together.

FIG. 7 shows both the maxillary and mandibular occlusion rims of a patient suitably contoured to establish the bite. Centric bite-lock sleeves 76 are shown in FIGS. 7a-8b and these plastic sleeves 76 are suitably cemented into the occlusion rims using soft plastic so that they can be subsequently employed for reassembling the maxillary and mandibular occlusion rims, in precisely the same relationship. A rim with teeth 78, as best shown in FIG. 8a, in the form of an outwardly extending flange help in anchoring the sleeve 76 into the occlusion rims. Bite-lock pins 80 extend through a locking disc 82 into the sleeves 76 for holding the occlusion rims together. Three discs are used, one in front of the occlusion rims and one on each side of the occlusion rims. (See FIG. 7). In order to ensure accurate alignment at all times, the outer ends of pins 80 are instantly cast in a plaster material so that they are immovable other than together as a unit as shown in phantom in FIG. 8b.

Figure 9:
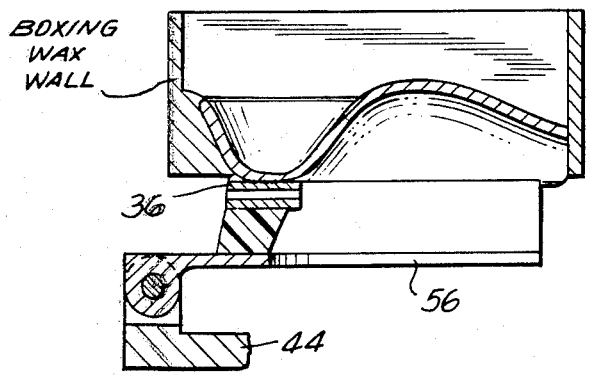
FIG. 9 is a side elevational view, similar to that of FIG. 6, without the ramp and sliding plate and the sliding pointer spear, but with a wax wall around the upper impression into which the maxillary cast is poured to obtain a final cast.
Figure 8B:
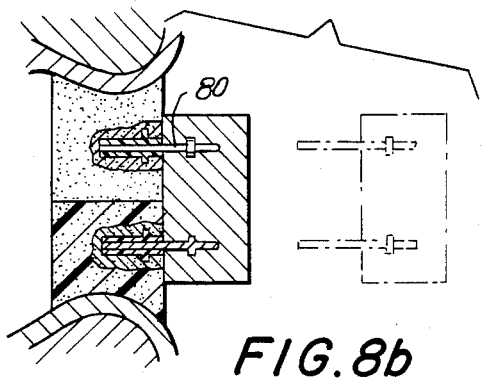
FIG. 8b illustrates the pins and cast material being removable as a unit.
Figure 10:
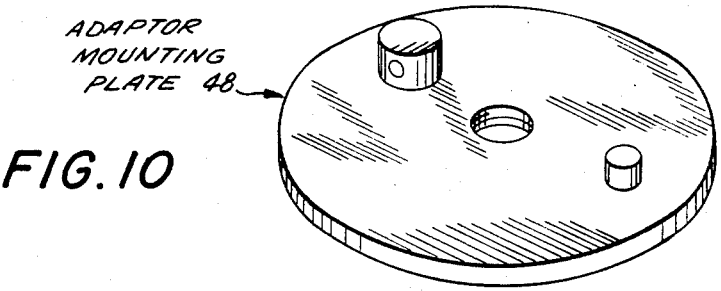
FIG. 10 is a mounting plate which may be used to adapt the apparatus to other articulators, facilitating the mounting of the tabletop and its base to the other well known articulator.

FIG. 9 illustrates a boxing around the impression for purposes of pouring a plaster stone material. When hardened, a cast is obtained; FIG. 10 represents an articulator adapter plate which is used in conjunction with certain types of articulators, the projections aligning with the mating base.

Figure 11:
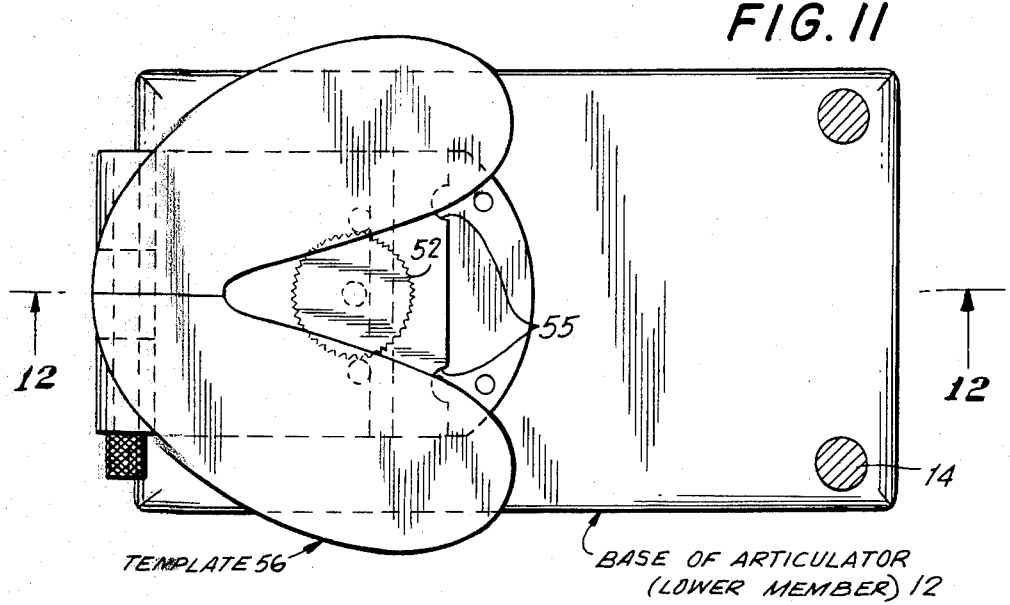
FIG. 11 is a plan view of an articulator shown in FIG. 12.
Figure 13:
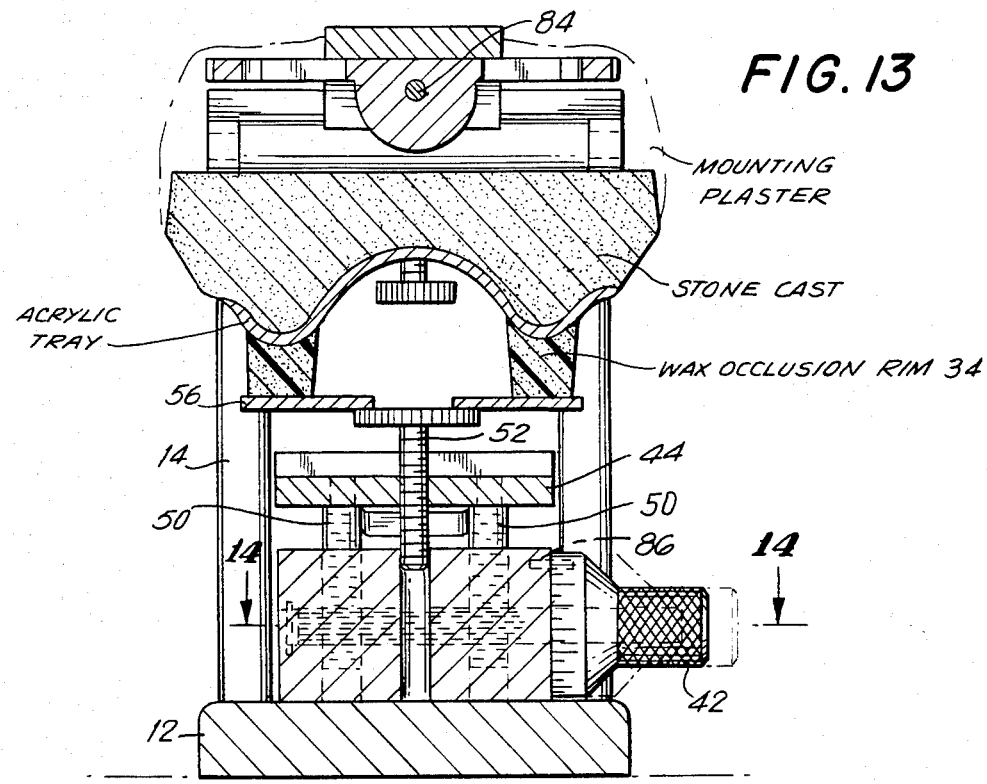
FIG. 13 is a cross-sectional view along the line 13—13 of FIG. 12.

FIGS. 11-13 show my apparatus with an articulator and with the upper member of the articulator holding the maxillary cast and being rotated upwardly, as shown in phantom. A suitable release pin 84 when pulled out, releases the entire upper mounting ring together with the mounted cast from the upper member of the articulator. FIG. 14 simply shows knob 42 released from the locking pin 86 by being pulled outwardly. Thereafter, raising and lowering of the tabletop 44 is achieved by rotation of the knob 42.

Figure 15:
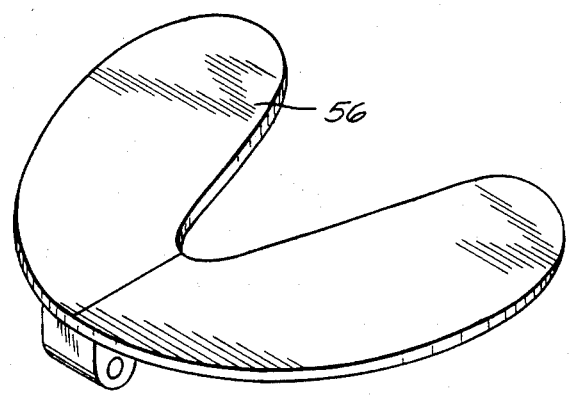
FIG. 15 is a perspective view of a "curved" template which is pivotably attached to the tabletop.

FIG. 15 represents a 20° template, curved anterior-posteriorly and transversely to reflect the curves of Spee and Wilson.

Figure 16:
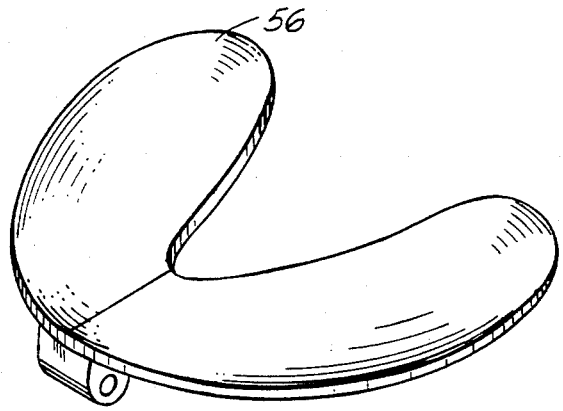
FIG. 16 is a perspective view of a "flat" template.
Figure 17:
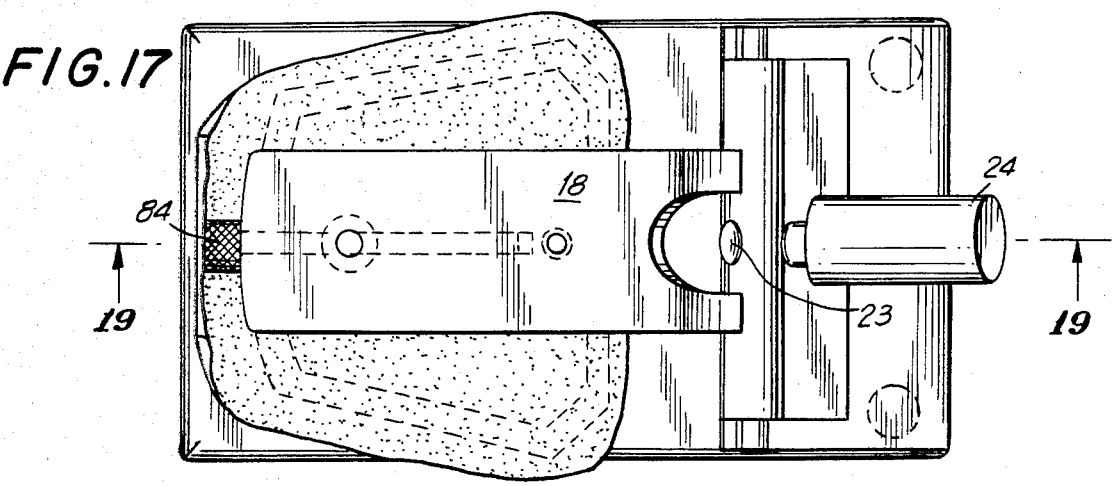
FIG. 17 is a plan view of an articulator shown in FIG. 19 with the upper cast with teeth set up and a lower cast with an occlusion rim, both mounted thereon.

FIG. 16 is a flat plane template. The correct template must be used according to the manufactured teeth chosen. Thus, depending on whether "flat plane", "full anatomic", or one of the semi-anatomic artificial teeth are used determines which template is to be utilized.

Figure 18:
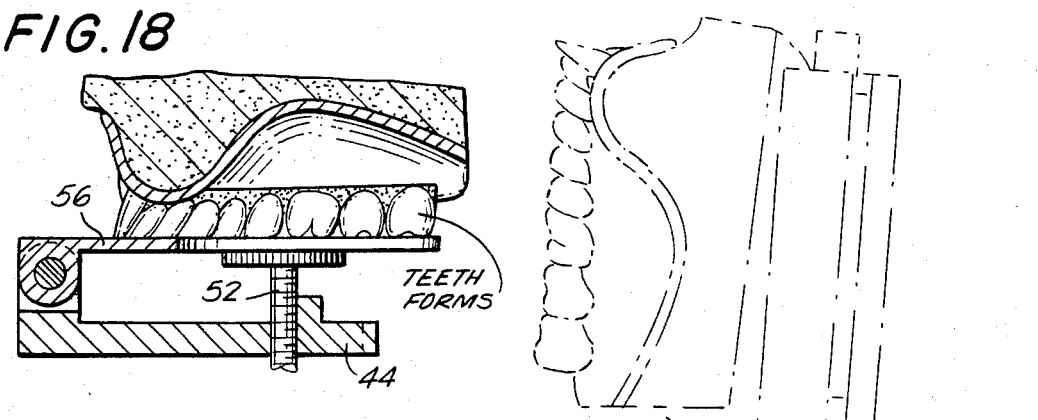
FIG. 18 is a fragmentary sectional view of the tabletop with template and upper teeth set up on the cast, against the template.

FIG. 18 illustrates the upper set up against the template and FIG. 19 shows the upper set up against the lower occlusion rim.

Figure 21:
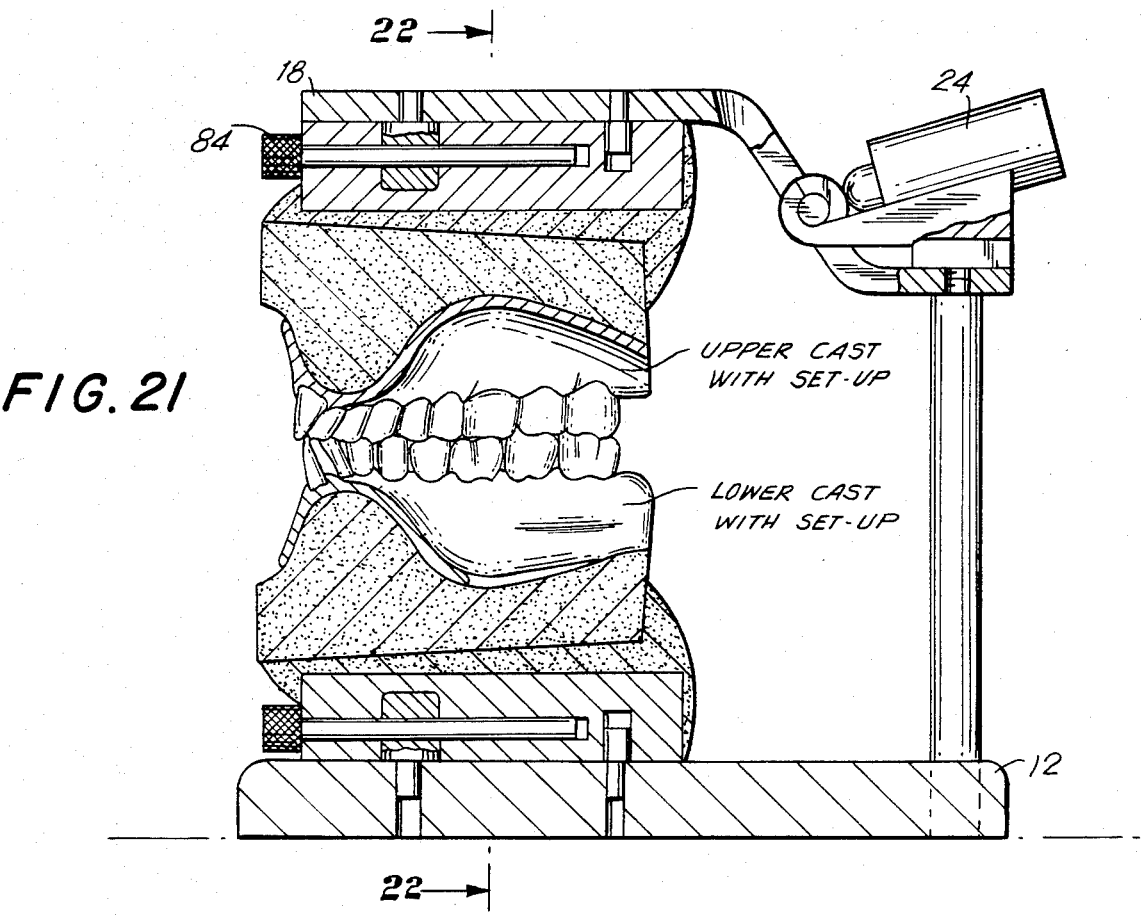
FIG. 21 is a side elevational view in cross-section of the articulator with both the upper and lower casts and set ups mounted thereon.
Figure 20:
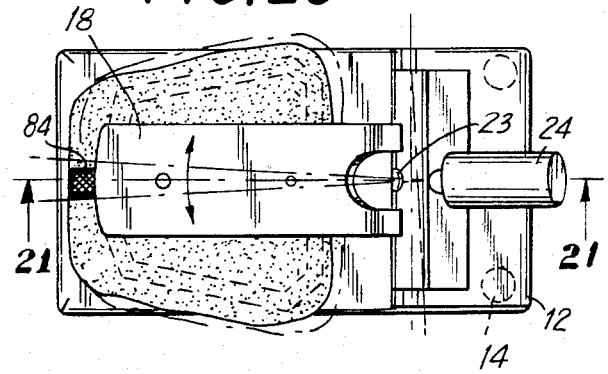
FIG. 20 is a plan view of the articulator of FIG. 21 showing the rocking of the maxillary set up relative to the stationary occlusal template for purposed of adjusting the balance of the teeth.
Figure 22:
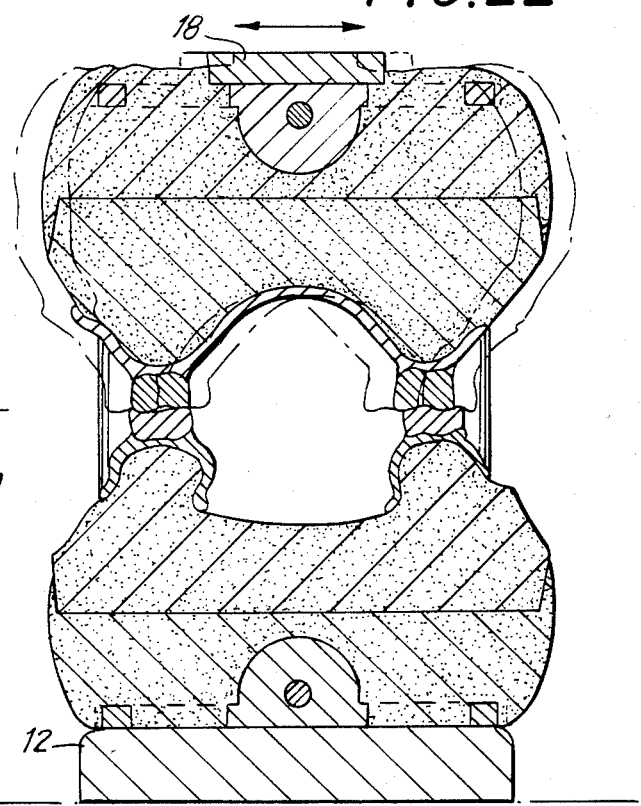
FIG. 22 is a cross-sectional view taken along the line 22—22 of FIG. 21.

FIGS. 20-22 show the dental prosthesis being rocked on the articulator to correct for balance of the teeth.

The ramp 60 is suitably provided with markings on both sides, and as the thumb screw wheel 61 is turned counter clockwise, the box will rise along with the sliding spear pointer 38. Such knife-edge unit 54 and spear are used for positioning the maxillary cast preparatory to being mounted on the articulator. The mounted cast is horizontal to the transverse plane as is a template underneath by manufacturing design. The knife edges 53 may be vertically adjustable as shown in FIG. 1 where suitable height markings are shown and a reference mark is provided on the leg portion 57' with screw means 57 for holding in place the elevated knife edges.

The knife edges 53 are suitably joined together by bridge means 53' which may be conveniently placed on any side of the knife edges 53. In addition, downwardly extending vertical leg portions 57' ride in suitable grooves or notches 57" and the screw head of said screw means 57 locks in position the knife edges 53 at a desired elevation.

OPERATION OF THE APPARATUS OF THE INVENTION

At the patient's first visit, make preliminary upper and lower impressions, establish maxillary low lip line (LLL) by using Ridge Lap Ruler (66) (see FIGS. 2-3). This measurement is in millimeters as are all markings or calibrations on the apparatus itself.

Following the making of the preliminary impressions, casts are poured and an acrylic tray is made on each. The mandibular tray receives a wax occlusion rim; the maxillary cast and tray receive special attention.

SPECIAL TREATMENT OF MAXILLARY CAST

A pencil trace is made on the entire maxillary cast along the muco-buccal fold including right and left tuberosities. Another trace must be made on the entire crest of the ridge on the cast.

This trace extends posteriorly and blends into the Pterygomandibular ligament on each side. The midsagittal plane line is also traced along palate of the cast onto the cast of the ridge anteriorly and the trace is extended onto the "art border". Points are thus established in each of the hamular notches by the intersection of the trace lines (called Posterior Identification Points—P.I.P.'s), and the intersection of lines anteriorly establishes the Anterior Identification Point (A.I.P.). The two Posterior Identification Points are connected by means of a slight cut or notch made in the cast, suitably by means of a saw, the "art border" not being disturbed. A prefabricated plastic mounting sleeve is pushed onto the spear FIG. 1 (36 pushed onto 38). The mounting sleeve raises the elevation of the upper surface of the pointer (38) 2-3 mm above the elevation of the knife edge (53) when sliding ramp (64) is in fully closed position in ramp (60).

SPECIAL TREATMENT OF MAXILLARY TRAY

In the area of the AIP, an opening is cut in the tray, larger than the mounting sleeve. Removed from the posterior segment of the tray is any material covering the PIP's. Take a prefabricated mounting sleeve 36 and push onto spear 38. Take knife edge unit FIG. 1 with sliding plate 64 fully closed in ramp 60 and turn upside down so that knife edges 53 engage in the cuts in the notches that were made in the maxillary cast previously by the saw. By moving knife edges right and left, and by sliding the pointer back and forth, we "cross hair" the mounting sleeve to be centered over the mid-sagittal plane line with point of spear 38 over and slightly anterior to AIP (FIG. 4). When so positioned, seal mounting sleeve to tray by closing hole in tray with acrylic, making for a chemical union of sleeve and tray. The formed acrylic tray is removed from the cast, then trimmed and polished.

A maxillary occlusion rim is luted to the acrylic tray and carved so rim is about 5 mm wide anteriorly and 8 mm wide posteriorly, with the distance from spear hole in anterior wall of tray to lower edge or rim being about 2 mm in excess of desired measured distance of patient as determined by Ridge-Lap ruler. The mounting sleeve is now impaled onto the spear, and the template surface is heated to a wax melting temperature. The occlusion rim is now suitably lowered on the apparatus until it touches the hot template. The template is held horizontal by resting on the heads of the lock pins. By moving the occlusion rim back and forth on the horizontal (with the sleeve impaled on the sliding pointer to rub the rim back and forth) while continuing to lower the rim by turning the wheel 61 clockwise, so that wax is melted off until the occlusion rim anterior Lower Lip Line (LLL) is at the measured distance of the patient. The template is, of course, heated as is necessary by suitable means, such as a bunsen burner (not shown). The tray with its occlusion rim is removed from the apparatus for patient try-in. The maxillary occlusion wax rim is carved to support the upper lip for proper fullness, to establish incisal edge of anterior maxillary incisors and to establish antero-posterior inclination of slope of occlusal plane to follow ala of nose-tragus of ear plane.

Alternately, the template may comprise part of an electrical heating circuit in which suitable connectors, such as the heads (one shown) 59' of the locking pins 59 or connecting terminals in the cradle are wired to an AC or DC source for bringing the template to a wax melting temperature. This set up is preferably the best as it is continuous, whereas with the bunsen burner the heat is intermittent.

For the patient's second visit, both maxillary and mandibular trays must be ready, the latter of which is similarly made, except that the mandibular occlusion rim is carved to the maxillary rim in the mouth. Border determinations on the trays are made and final impressions are also made. The maxillary occlusion rim is checked against the ala of nose-tragus of ear line for parallelism, and the mandibular occlusion rim is carved to be parallel to the same plane. Also, at this time, vertical dimension and centric relation are established. The centric relation is recorded by placing the centric bite-lock sleeves into both the maxillary and mandibular rims, and locking them to the trays with a fast-setting acrylic. To insure parallelism of the sleeves when set, the locking disc or bite-lock jig is employed with the pins 80 engaging the sleeves through the bit-lock jig. A pick-up impression of the bite-lock pins is taken with the patient in centric relation using copper bands suitably filled with any rigid pick-up material, such as impression plaster, silicon putty, or other like compounds. Upon removal of the bite-lock pins, trays and rims are taken from the mouth, and the patient is dismissed.

Using the apparatus, one now determines which template is to be employed depending upon the desired occlusion, and with the sliding plate 64 with the spear/pointer 38 raised to its highest elevation the mounting sleeve of the impression tray is impaled. The tray is lowered until its occlusion rim rests on the template, and one then records the ramp mark reading. A trace is now made on the template of the patient's arch form using a calcium hydroxide base material diluted with water. The impression is then boxed and placed with the apparatus on a vibrator to pour the final cast. Then this poured cast, tray and apparatus are placed on an articulator.

With the calibrated adjustor knob of the apparatus in the "zero position", maximum movement of the tabletop is thus available after the maxillary cast is mounted with plaster to the upper mounting ring 20, on the upper member 18. When mounting of maxillary cast is completed, the articulator cannot be opened unless the spear is first removed from the mounting sleeve, otherwise it can be damaged by bending. When the upper member of the articulator is swung open, the entire apparatus is now removed from the articulator. The boxing wax is removed from the upper cast and the occlusion rims (upper and lower) are reassembled in centric relation by means of the bite-locks. The mounted upper cast together with the mounting ring is also removed from the articulator and placed upside down on a bench. The lower tray with the mandibular impression therein is boxed. The whole assembly is then placed on a vibrator for the lower cast to be poured. After the poured lower cast is set, the entire assembly is replaced right side up on the articulator, and with the upper member of the articulator swung out of the way, a mound of plaster is placed on a lower mounting ring. Then, by returning the upper member to its horizontal position, the lower cast is thus mounted to the articulator base, while it is still attached to the upper cast in centric relation. The bite-locks must now be removed in order to open the articulator. The boxing wax is removed from the lower cast. The mounted mandibular cast is removed from the articulator and the base means sans knife edge unit, with tabletop and template bearing tracing of patient's arch form replaced on the articulator. The template is inclined to follow the maxillary occlusion rim and such template inclination is supported by the threaded and knurled headed screw, because the knife edge unit has been removed. In all cases where the apparatus is used and the patient is without gross deformities of head and/or face, this plane will be parallel to the bench top and to the upper and lower members of the articulator.

The occlusion rims and trays are now removed from the casts and new trays are made. On the maxillary tray, set up maxillary teeth against the template. Then remove the apparatus and replace it with the mounted mandibular cast and tray. The mandibular teeth are set up against the maxillary teeth.

The patient's third and last visit need not really be necessary unless the dentist or technician desires to confirm all steps of the prosthetic construction. Should it be desired to change the plane of occlusion, the apparatus will permit a movement of plus or minus 4 mm on the vertical. Thus, a turn of one marking to the next mark on the adjustor knob will make a 1 mm change in vertical level of the tabletop.

The waxed-up mandibular cast is removed from the articulator and replaced with the apparatus including knife edge unit but sans template with the knife edge unit at the previously recorded ramp elevation. Excess wax is added posteriorly to the waxed up maxillary set up so that the wax will rest on the knife edge. The pointer is then advanced to pierce a small mound of wax anteriorly, making a hole in the palatal wax-up of the maxillary set-up. After the hole is made, the pointer is retracted, the articulator is opened, the mounted maxillary cast is removed. Both dentures can now be flasked and further processed. After the dentures are processed, the maxillary denture is again supported on the apparatus by the posterior acrylic grooves made during wax-up and front supported by pointer in the hole. With the denture so oriented, any undercuts of the denture can be relieved, and a cast can be poured and mounted to the articulator. After the upper denture is thus mounted to the articulator, remove knife edge unit from apparatus and reposition template on apparatus. Bring template in contact with the teeth. The teeth of the maxillary denture can be ground against the template using thin articulating paper to correct any centric prematurities. This denture can then be finished and polished prior to placement into the patient's mouth. At this time, the lower denture already polished, is also placed in the patient's mouth and is ground against the upper denture to complete and correct the prostheses as may be necessary.

The occlusion rims as is well known and conventional serve the purpose of indicating where the edges of one's teeth will be in all planes, and they eventually serve as the medium which will hold the teeth for the upper and lower set-ups. The teeth which are conventionally supplied and purchased in matched sets are individually placed into the rim to form a partial or complete denture.

With the apparatus of the invention, the number of patient's visits is cut from today's requirement of about five to six visits to about a maximum of three visits.

Even two visits are sufficient as the third one can be dispensed with in many cases as it is a try-in visit and is simply used to confirm the prosthetic construction. Such a reduction in time and labor reduces costs of the dentures and thus contribute to minimizing laboratory errors. In fact, less experienced laboratory personnel can be employed to make the preliminary, as well as the final casts and perform the various other laboratory procedures, such as adapting the upper and lower acrylic trays which are made to the final casts and the building of the wax occlusion rims and carving same, except that the mandibular occlusion rim is carved to the maxillary rim in the mouth by the dentist.

The device of the invention, like my earlier apparatus, does not require the use of a face bow by the dentist, nor is the use of cephalometric x-ray analysis required. These earlier studies and methods for mounting of the maxillary casts are not precise or exact and lend themselves to many errors. With the precision instrument of the present invention, there is less chance of any errors as no other studies or analysis or auxiliary tools need be employed, except for my Ridge Lip ruler which is used to measure the lower lip line (L.L.L.). Incidentally, the ruler can be made to be disposable or preferably made of a suitable metal, such as stainless steel so that it is capable of being sterilized for repeated use. The flexible ribbon at the end of the ruler may be suitably made of a material such as copper and the like.

It should also be recognized that although a mounting spear is shown employed with the apparatus of the invention, it can be dispensed with inasmuch as the knife edges can be raised to an amount or distance to account for the distance between the hamular notches and the bottom of the occlusion rim. However, in order to raise the knife edges the necessary distance, one initially must measure or scale off the width of such space or distance, and this can be easily done with any convenient tool in hand, such as a ruler, tongue depressor, etc. With such step, the cast need not be mounted by a mounting sleeve. By raising the knife edges to the desired height, one can set up the naked cast even more quickly and efficiently so that is properly located on the apparatus.

Although the present invention has been described in some detail by way of illustration and example for purposes of clarity of understanding, it will, of course, be understood that various changes and modifications may be made in the form, details, and arrangements of the parts without departing from the scope of the invention as set forth in the following claims:

I claim:

1. A device for use in the construction of dental prostheses embodying impression trays and poured casts, comprising:

a base adapted to be placed on an articulator, a tabletop on said base, the height of which is adapted to be adjustable; a removable template adapted to be pivotably mounted to a cradle provided on said tabletop; a knife edge unit having spaced apart knife edges, and a spear box and pointer adapted to be raised or lowered, a ramp, including a track having a sliding plate for carrying and for guiding the movement of said spear and box pointer, carried on said knife edge unit and a cooperatively associated adjustment screw for raising and lowering said spear box and pointer; said knife edge unit being removably attached to said base; and said spear box being guided for movement along said ramp by threaded means in an inclined sloped direction.

2. The device according to claim 1, wherein the adjustable tabletop is associated with a calibrated knob and rack and pinion means for controlling the height of said tabletop.

3. The device according to claim 2, wherein the calibrated knob which raises or lowers the table-top is self locking to maintain a desired elevation by having the underside of the knob fitted with spaced holes to engage a pin press fitted into said base.

4. The device according to claim 1, wherein said pointer is adjustably positionable horizontally between said spaced apart knife edges.

5. The device according to claim 1, wherein said knife edge unit is removably mounted to said base by means of locking pins.

6. The device according to claim 1, including threaded means having an enlarged head in said base for securing said knife edge unit to said base.

7. The device according to claim 6, wherein said threaded means also serves to position the inclination of said template.

8. The device according to claim 1, wherein said knife edges may be adjusted in height independently of said knife edge unit mounted on the base.

9. The device according to claim 8, wherein each of said knife edges is provided with adjusting means for vertically adjusting the height of said knife edges.

10. The device according to claim 1, including a sleeve for the pointer of said spear box for incorporation into the tray in which an impression can be made or in which a cast may be placed.

11. The device according to claim 10, wherein the sleeve's thickness is such that it slightly raises the maxillary cast anteriorly when the casted acrylic spear mold and tray is impaled on said pointer.

12. The device according to claim 1, wherein said cradle is mounted to said table-top in a manner which permits adjustment of said template in a side to side fashion.

13. The device according to claim 12, wherein said adjustment is provided by means of slots in said tabletop and threaded means fastened to said cradle and extending through said table-top.

14. The device according to claim 1, including electrical circuit means connected to said template for heating same in a continuous manner to a wax melting temperature.

* * * * *